United States Patent [19]

Schmuhl

[11] Patent Number: 5,135,191
[45] Date of Patent: Aug. 4, 1992

[54] MEDICAL SUPPORT SYSTEM
[75] Inventor: James M. Schmuhl, Brandon, Wis.
[73] Assignee: JAGCO Corporation, Brandon, Wis.
[21] Appl. No.: 697,686
[22] Filed: May 9, 1991
[51] Int. Cl.⁵ .................................................. A47G 29/00
[52] U.S. Cl. ........................................ 248/125; 5/658;
248/129; 403/109; 403/362
[58] Field of Search ............... 248/125, 121, 122, 129,
248/150, 158, 218.4, 220.2, 229, 230, 316.1,
316.2; 403/109, 362; 5/503; 280/304.1

[56] References Cited
U.S. PATENT DOCUMENTS

| | | | |
|---|---|---|---|
| 2,696,963 | 12/1954 | Shepherd | 248/229 |
| 3,317,168 | 5/1967 | Ziph | 248/125 X |
| 3,835,486 | 9/1974 | Benoit et al. | 5/503 |
| 4,332,378 | 6/1982 | Pryor | 248/125 X |
| 4,511,157 | 4/1985 | Wilt, Jr. | 248/125 X |
| 4,767,131 | 8/1988 | Springer et al. | 280/304.1 |
| 4,878,685 | 11/1989 | Bahm | 280/304.1 |
| 4,945,592 | 8/1990 | Sims et al. | 5/503 X |
| 4,966,340 | 10/1990 | Hunter | 248/125 |
| 5,016,307 | 5/1991 | Rebar | 5/503 |

Primary Examiner—Ramon O. Ramirez
Attorney, Agent, or Firm—Donald Cayen

[57] ABSTRACT

A medical support system comprises a pole for supporting intravenous related medical equipment. The pole has two different diameters to enable it to be interchangeably inserted into a wheeled strand, a wheelchair bracket, and a gurney cart socket. A stop in the stand limits insertion of the pole into the stand, and a locking knob locks the pole to the stand. The pole and the stand are designed to enable the pole to be inserted into and withdrawn from the stand under normal ceilings without having to tip the stand. The wheelchair bracket receives and locks the pole in a manner similar to the stand. The medical support system enables a patient connected to the intravenous related medical equipment to be transported in a wheelchair or gurney cart without also having to transport the stand.

11 Claims, 2 Drawing Sheets

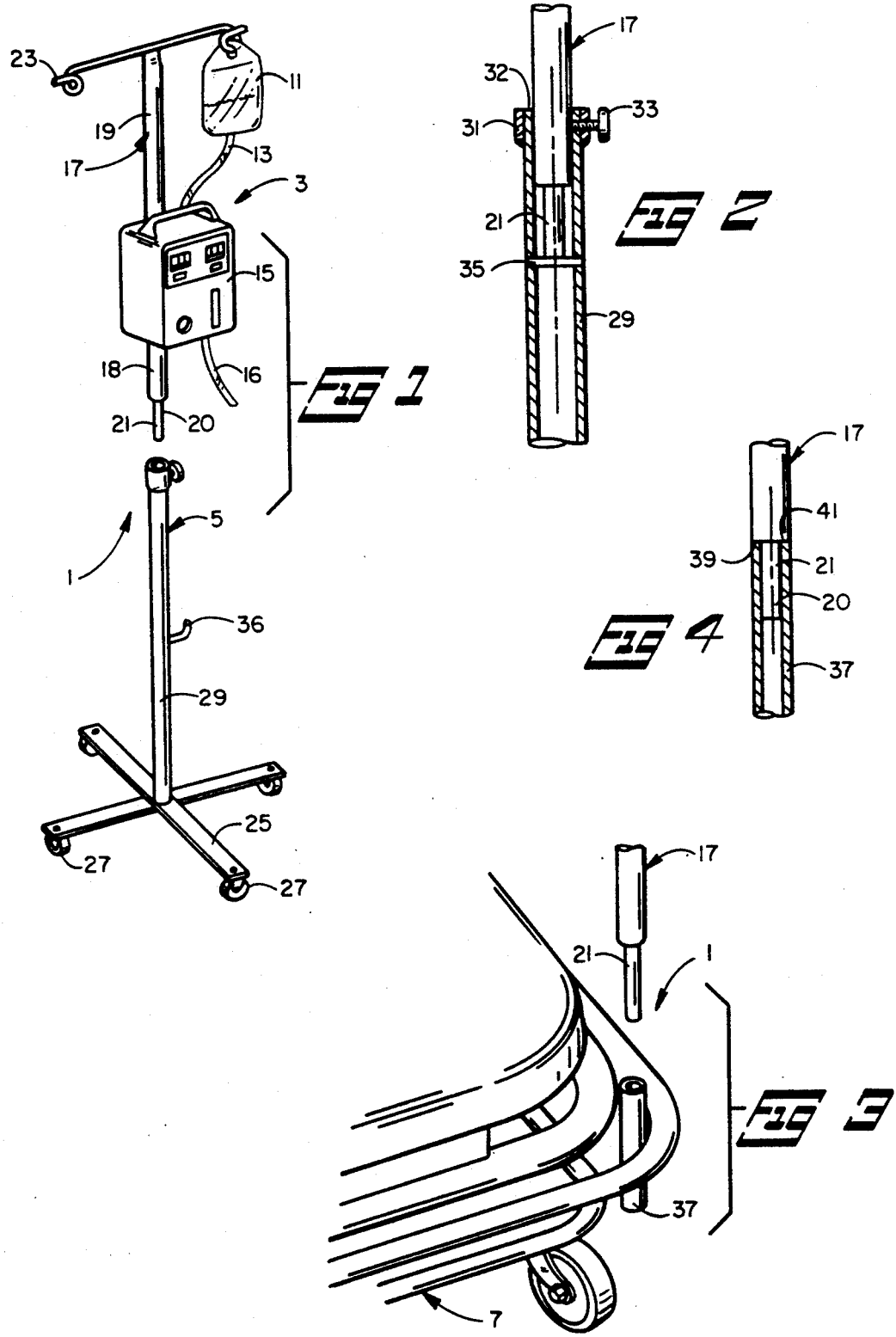

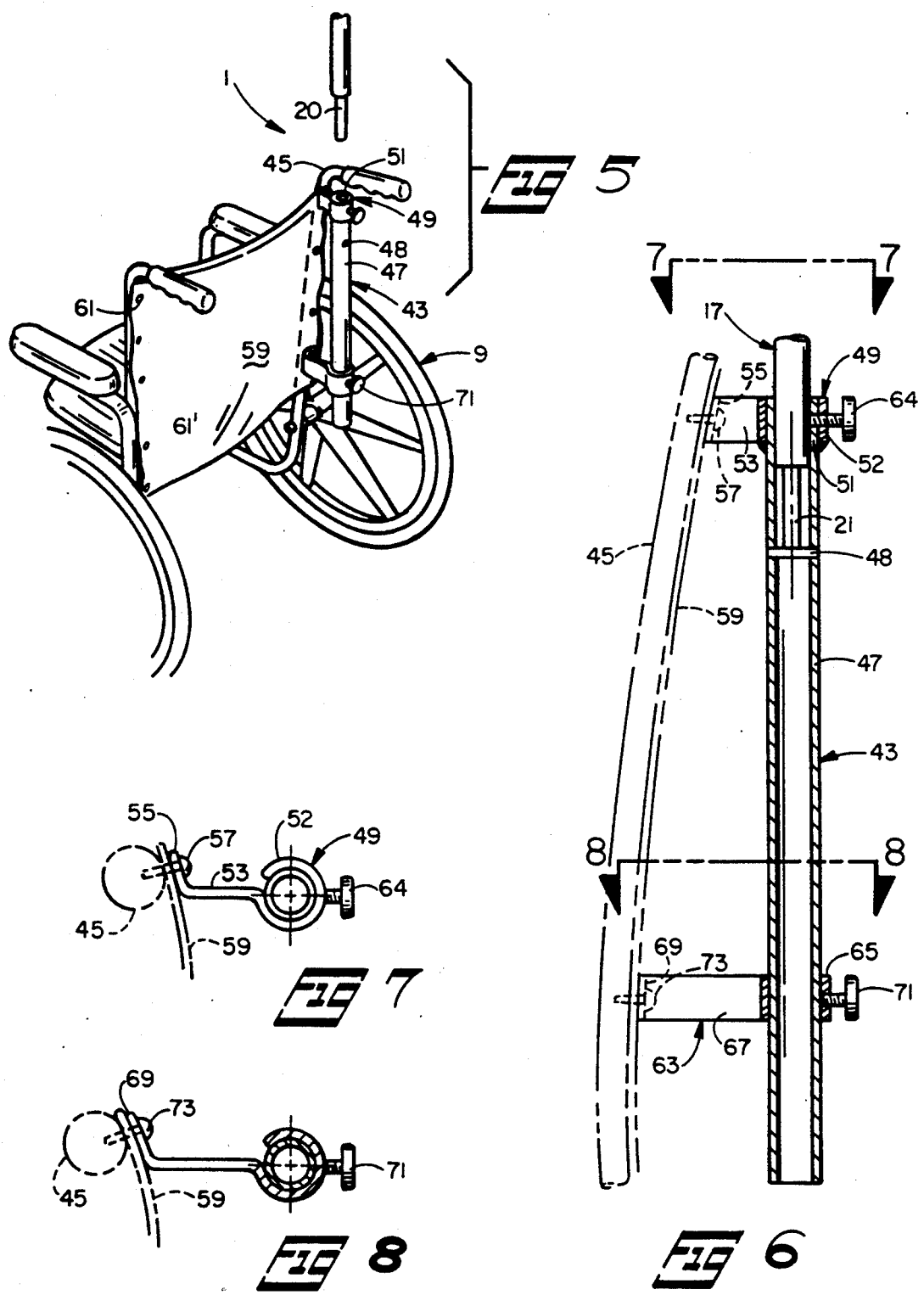

MEDICAL SUPPORT SYSTEM

BACKGROUND OF THE INVENTION

1. Field of the Invention

This invention pertains to medical equipment, and more particularly to apparatus related to intravenous feeding.

2. Description of the Prior Art

In the process of supplying nutrition and fluids to patients by intravenous means, it is known to suspend a fluid-holding bag from an intravenous stand. The stand supports the bag close to the patient at all times. It is further known to pass the intravenous fluid through a combination pump and monitoring device interposed between the intravenous bag and the patient. The pump-monitor is usually mounted to the same stand as the bag.

Prior intravenous stands include a wheeled base with an upright tube fixed thereto. The tube is usually approximately four feet long. A rod that normally has a diameter of approximately one inch and is approximately four feet long fits inside and is supported in the stand tube such that approximately three to four feet of the rod extend out of the tube. The exposed end of the rod is usually designed with a cross arm for holding the intravenous bag. The combination pump-monitor is normally clamped to the tube of the stand in order to keep the center of gravity of the pump-monitor as low to the floor as practical and thus contribute to the stability of the stand.

A patient connected to an intravenous bag is somewhat restricted in her activities because the stand and bag must accompany her wherever she goes. If the patient is ambulatory, she merely pushes the stand with her as she walks about. However, a problem arises with non-ambulatory patients. In those situations, an attendant is required to push the patient in a wheelchair or gurney cart. The attendant must then handle two awkward items: the wheelchair or gurney cart and the stand. To assure that the intravenous tube does not pull on the patient, the attendant must constantly exercise care to keep the stand very close to the wheelchair or gurney cart. As a result, transporting the patient is a time consuming and even hazardous task. In many cases, safe transportation of the patient requires that her wheelchair or gurney cart and the stand be pushed by two different attendants. That practice represents an inefficient use of personnel.

To overcome the problems associated with transporting both a gurney cart carrying a patient and an intravenous bag for the patient, many gurney carts are equipped with a socket for holding the rod of an intravenous stand. The intent is that the rod can be removed from the tube of the stand base and inserted into the gurney cart socket. Then both the patient and her intravenous equipment can be transported on only the gurney cart.

However, in practice that solution rarely works. That is because invariably the gurney cart socket and the stand rod have different diameters. The gurney cart sockets are sized to fit a rod having a diameter of approximately 0.50 inches. That size rod is satisfactory to hold an intravenous bag, but it is too small to properly hold a pump-monitor unit. Accordingly, as mentioned, prior intravenous stands invariably have one inch diameter rods with correspondingly sized tubes for holding the rods, and 0.50 inch diameter rods are only rarely used in hospitals. Consequently, the great majority of intravenous rods in present use will not fit in the gurney cart sockets. Even if a rod is used that is interchangable between the prior intravenous stands and gurney carts, the pump-monitor unit must be unclamped from the stand tube and reclamped to the rod each time the rod is transferred from the stand to the gurney cart.

A further problem related to prior intravenous stands is that their rods are not designed to be easily removed from the stand tubes. The long length of approximately four feet makes a rod impossible to withdraw from a stand tube without tipping the stand base such that the rod clears the room ceiling. Removing a stand rod is thus awkward and even difficult for an attendant to perform alone, especially with an intravenous bag mounted to the rod. For practical purposes, then, the rod is a permanent part of the stand, with the previously explained disadvantages associated with that construction.

Thus, a need exists for improvements in supports for intravenous related equipment.

SUMMARY OF THE INVENTION

In accordance with the present invention, a versatile medical support system is provided that carries intravenous bags and associated equipment to suit different modes of patient transportation. This is accomplished by apparatus that includes an elongated pole that is interchangeably supportable in intravenous stands, gurney carts, and wheelchairs.

The pole has two cross sections. The first cross section, which extends for the majority of the pole length from its upper end, is of sufficient size to enable a conventional intravenous pump-monitor to be mounted to it. The pole upper end has cross arms for hanging an intravenous bag. The pole lower end has a smaller cross section that fits within the sockets of conventional gurney carts. The pole has an overall length of approximately three feet.

To support the pole in an intravenous stand, the stand comprises a wheeled base and a tube upstandingly fixed to the base. The tube has an overall height of approximately three feet. The relatively short height of the tube of the stand of the present invention enables the pump-monitor to be mounted to the pole while providing the same stability as was possible with prior stands only by mounting the pump-monitor to the stand tube. The tube upper end is configured to accept the pole lower end and to accept and guide a portion of the pole first cross section. In addition, the tube upper end includes a stop that limits the amount of insertion of the pole into the tube and a clamp that clamps the pole within the tube. The limited insertion of the pole into the tube and the relatively short lengths of the tube and pole enable the pole upper end to easily clear a room ceiling when the pole is withdrawn from the stand tube. As a consequence, the problems associated with removing the rods from prior intravenous stands are eliminated. In that manner, the pole of the present invention with the intravenous related components mounted thereon can be readily transferred between an intravenous stand and a gurney cart.

To enable the intravenous equipment to be transported on a wheelchair, the present invention further comprises a bracket designed to be permanently mounted to a wheelchair and to hold the pole. The bracket is manufactured with an elongated post and a pair of braces that extend at approximately right angles to the post. The first brace is secured to the upper end of the post. The second brace is captured on and is slidable along the post. Both braces have feet that are fastenable to a selected vertical frame member of the wheelchair so as to position the post in a substantially vertical attitude. For example, the braces may be mounted to the vertical member that supports the wheelchair back. To accommodate the contour of wheelchair frame members and enable the bracket post to be vertical, the second brace is longer than the first brace.

To mount the bracket to the wheelchair, the foot of the first brace is fastened to the upper end of the wheelchair vertical member. The post is held vertical, and the second brace is slid along the post until its foot is at a location whereat it can be fastened to the wheelchair.

The upper end of the bracket post is designed in a manner similar to the upper end of the stand tube; the bracket post includes a depth stop for the pole and a pole clamp. In that manner, the pole is interchangeably insertable into the stand tube, the wheelchair bracket, and the gurney cart socket. The result is that a hospital attendant can easily transfer intravenous related equipment between a stand, wheelchair, and gurney cart.

Other advantages, benefits, and features of the invention will become apparent to those skilled in the art upon reading the detailed description of the invention.

BRIEF DESCRIPTION OF THE DRAWINGS

FIG. 1 is a perspective view of a portion of the medical support system of the present invention.

FIG. 2 is an enlarged cross sectional view of the mounting between the intravenous stand and pole according to the present invention.

FIG. 3 is a partial perspective view of a gurney cart equipped with a socket for receiving the pole of the present invention.

FIG. 4 is an enlarged cross sectional view of the mounting between a gurney cart socket and the pole of the present invention.

FIG. 5 is a perspective view of a wheelchair equipped with a bracket for receiving a pole according to the present invention.

FIG. 6 is an enlarged cross sectional view of the wheelchair bracket of the present invention with a pole inserted therein.

FIG. 7 is a cross sectional view taken along lines 7—7 of FIG. 6.

FIG. 8 is a cross sectional view taken along lines 8—8 of FIG. 6.

DETAILED DESCRIPTION OF THE PREFERRED EMBODIMENT

Although the disclosure hereof is detailed and exact to enable those skilled in the art to practice the invention, the physical embodiments herein disclosed merely exemplify the invention, which may be embodied in other specific structure. The scope of the invention is defined in the claims appended hereto.

Referring to FIGS. 1, 3, and 5, a universal medical support system 1 is illustrated that includes the present invention. The medical support system is particularly useful for interchangeably supporting intravenous related equipment 3 in a stand 5, a gurney cart 7, and a wheelchair 9. However, it will be understood that the invention is not limited to medical related applications.

The intravenous equipment 3, which forms no part of the present invention, typically includes a flexible bag 11 that holds a selected fluid. A flexible tubing 13 leads from the bag 11 to a conventional combination pump-monitor device 15. The pump-monitor device 15 accurately meters fluid from the intravenous bag to an outlet tubing 17, which leads and connects in known manner to a patient, not shown.

In accordance with the present invention, the intravenous bag 11 and pump-monitor 15 are mounted to a pole 17 that is interchangeably transportable by the stand 5, gurney cart 7, and wheelchair 9. The pole 17 is preferably approximately three feet long and has two different cross sections. The first cross section 18, which extends for most of the length of the pole, has a diameter of at least one inch. The second cross section 20, which is approximately four inches long at the lower end 21 of the pole, has a diameter of approximately 0.50 inches. A cross arm 23 is fixed to the pole upper end 19. The intravenous bag 11 is supported from the cross arm 23, and the pump-monitor 15 is attached to the pole at a location along the first cross section 18 as close as practical to the second cross section 20.

The stand 5 is comprised of a base 25 with conventional casters 27. A tube 29 is upstandingly fixed to the base 25. The length of the tube 29 is approximately three feet. The tube has an interior configured to receive the cross section 20 of the pole lower end 21 and also a portion of the pole first cross section 18.

Also looking at FIG. 2, a collar 31 is joined, such as by welding, to the outside of the upper end 32 of the tube 29. A threaded locking knob 33 mates with a tapped hole through the collar 31 and the tube. A stop, such as a pin 35, is built into the tube approximately eight inches below the tube upper end 32. A hook 36 may be welded to the tube for holding such items as a urine bag, not illustrated in the drawings.

The pole 17 with the intravenous bag 11 and pump-monitor 15 mounted thereon is inserted into the upper end 32 of the stand tube 29 until the pole end 21 rests on the pin 35. Then the locking knob 33 is rotated to lock the pole in place. The low center of gravity of the pump-monitor renders the stand 5 stable. The stand and pole are then ready to be pushed by a patient who is connected to the intravenous tubing 16 as she walks about.

Further in accordance with the present invention, the pole 17, together with the intravenous bag 11 and pump-monitor 15, is very quickly and easily removed from the stand 5 and inserted into a socket 37 that is joined to the gurney cart 7. Also see FIG. 4. The pole cross section 20 at the lower end 21 is designed to enter and to be snugly guided and retained in the gurney cart socket 37. The pole cross section 20 enters the socket 37 until the pole shoulder 39 rests on the upper end 41 of the socket. The pole is thus held firmly in place on the gurney cart. The present invention thereby enables an attendant to transport a patient who is connected to the intravenous tubing 16 on the gurney cart without also having to push along a stand 5. Such interchangeability between an intravenous stand and a gurney cart is rarely possible with prior stands. That is not only because of the incompatibility of the prior rods with the gurney cart sockets 37, but also because of the difficulty of removing the prior rods from the prior stand tubes. With the medical support system 1 of the present invention, on the other hand, the relatively short lengths of the tube 29 and the pole 17, together with the relatively short insertion distance of the pole into the stand tube 29 enables the pole to be withdrawn from and inserted into the tube without having to tip the stand.

It is a feature of the present invention that the pole 17 is interchangeably transportable by the wheelchair 9 in addition to the stand 5 and the gurney cart 7. Turning to FIGS. 5–8, the medical support system 1 includes a bracket 43 that is designed to be mounted to a vertical frame member 45 of the wheelchair. The bracket 43 is fabricated with a tubular post 47 that is generally similar to the tube 29 of the stand 5. A pin 48 or other stop extends transversely through the post 47 approximately eight inches below the post upper end 51. A first brace 49 is welded or otherwise secured to the upper end 51 of the post 47. In the illustrated construction, one end 52 of the first brace 49 wraps around the post and continues into a leg portion 53. The leg portion 53 terminates in a foot 55 that is shaped to fit the contour of the wheelchair vertical member 45. A screw 57 is used to attach the brace foot 55 to the wheelchair vertical member. I have designed the bracket to take advantage of holes pre-existing in most wheelchairs that are used to fasten the cloth back 59 to the wheelchair vertical member. The back 59 is sandwiched between the vertical frame member and the brace foot. In that manner, the bracket mounting screw 57 merely replaces one of the pre-existing screws 61, and no modifications to the wheelchair frame member are necessary. A locking knob 64 is threaded through the first brace end 52 and the post upper end 51.

The bracket 43 further includes a slidable brace 63. The slidable brace 63 has a first end 65 that wraps around the post 47 and that extends into a leg portion 67. The leg portion 67 terminates in a foot 69 that conforms to the cross section of the wheelchair vertical frame member 45. To suit the longitudinal contour of the vertical frame member of most wheelchairs, the leg portion 67 of the slidable brace 63 is longer than the leg portion 53 of the fixed brace 49. A locking knob 71 is threaded through the slidable brace first end 65.

The bracket 43 is mounted to the wheelchair 9 by removing a backing screw 61 at the top of the vertical frame member 45 and using the longer screw 57 to mount both the bracket brace 49 and the backing 59 to the vertical frame member. Then the slidable brace 63 is slid along the post 47 until the brace foot 69 is aligned with a backing screw 61' at the bottom of the vertical frame member. The screw 61' is removed, and a longer screw 73 is used to mount the brace to the vertical frame member with the backing 59 sandwiched therebetween. The locking knob 71 is tightened, and the bracket is firmly in place on the wheelchair. The different lengths of the two braces 49 and 63 enable the post to be substantially vertical when the braces are secured to the wheelchair vertical member.

The pole 17 is inserted into the wheelchair bracket 43 in the same manner as the pole is inserted into the stand tube 29, FIG. 2. The pole second end 21 is dropped into the bracket post upper end 51 until the pole contacts the bracket pin 48. After the locking knob 64 is tightened, the pole and its intravenous bag 11 and pump-monitor 15 are sturdily in place on the wheelchair. An attendant is then able to transport a patient who is connected to the intravenous tubing 16 in the wheelchair without having to also wheel along a separate stand 5.

Thus, it is apparent that there has been provided, in accordance with the invention, a medical support system that fully satisfies the aims and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A medical support system for use with a wheelchair and a gurney cart comprising:
   a. an elongated pole having first and second sections, the pole having a first predetermined diameter at the first section and a second diameter less than the first diameter at the second section, the pole first section supporting selected medical related components thereon;
   b. a stand comprising:
      i. a wheeled base;
      ii. a tube fixed to and upstanding from the base and having an upper end, the tube having an inner diameter slightly greater than the pole first diameter to enable the pole second section and a portion of the pole first section to be inserted into the tube;
      iii. stop means at a predetermined distance from the tube upper end for limiting insertion of the pole into the tube;
   c. a bracket comprising:
      i. an elongated post having upper and lower ends and an inner diameter slightly greater than the pole first diameter to enable the pole second section and a portion of the pole first section to be inserted into the post;
      ii. stop means at a predetermined distance from the post upper end for limiting insertion of the pole into the post; and
      iii. brace means for mounting the post in a substantially vertical attitude to a selected frame member of the wheelchair; and
   d. a socket joined to the gurney cart in a substantially vertical attitude, the socket having an inner diameter slightly greater than the diameter of the pole second section to enable the pole second section to be inserted into the socket,
   so that the pole is interchangeably insertable into the stand tube, wheelchair bracket, and gurney cart socket to enable a patient connected to the selected medical related components to be transported in the wheelchair or gurney cart without having to also transport the stand.

2. The medical support system of claim 1 wherein the brace means comprises:
   a. a first brace secured to the post upper end and having first leg means for mounting to the selected frame member of the wheelchair;
   b. a second brace slidable along the post and having second leg means for mounting to the selected member of the wheelchair; and
   c. locking means for releasably locking the second brace to the post at a selected location therealong suitable for mounting the second leg means to the selected member of the wheelchair.

3. The medical support system of claim 2 wherein the second leg means has a different length than the first leg means to thereby enable the bracket to accommodate a longitudinal contour of the selected member of the wheelchair and maintain the vertical attitude of the post.

4. Apparatus for transporting intravenous related medical equipment comprising:
  a. a stand comprising:
    i. a wheeled base;
    ii. a tube fixed to and upstanding from the base and having a predetermined inner diameter and length and a free end; and
    iii. a stop at a predetermined distance from the tube free end;
  b. a wheelchair bracket comprising:
    i. a post having an upper end and a lower end and an inner diameter substantially equal to the inner diameter of the stand tube;
    ii. brace means for mounting the post in a generally upright attitude on the wheelchair; and
    iii. a stop in the post at a predetermined distance from the upper end thereof; and
  c. an elongated pole having a first section for supporting the intravenous related medical equipment thereon and a second section, the pole second section and a portion of the pole first section being interchangeably insertable into a selected one of the stand tube and the bracket post until the pole second section contacts the stop in the stand tube or the bracket post to thereby enable a person connected to the intravenous related medical equipment to be transported in the wheelchair independently of the stand.

5. The apparatus of claim 4 wherein the wheelchair bracket brace means comprises:
  a. a first brace secured to the post, the first brace having first leg means for mounting at a first selected location to the wheelchair; and
  b. a second brace slidably captured on the post and having second leg means for mounting to the wheelchair at a second location selected to enable the first and second braces to position the post in the generally upright attitude.

6. The apparatus of claim 5 wherein the first and second leg means are of unequal length to thereby enable the bracket to be mounted on a contoured wheelchair.

7. Apparatus for transporting a patient on a gurney cart while the patient is connected to intravenous related medical equipment comprising:
  a. an elongated pole having a first section configured to support the intravenous related medical equipment and a second section configured for inserting into a selected socket of the gurney cart; and
  b. a stand comprising:
    i. a wheeled base;
    ii. a tube upstanding from the base and having an inner diameter configured to receive the pole second section and a portion of the pole first section; and
    iii. stop means in the tube for limiting the amount of insertion of the pole into the tube,
  so that the intravenous related medical equipment can be supported on the pole first section, and the pole second section and a portion of the pole first section can be removably inserted into the stand tube and the pole second section can be removably inserted into the gurney cart socket to thereby enable the patient connected to the intravenous related medical equipment to be transported on the gurney cart without transporting the stand.

8. A bracket for supporting a pole with intravenous related medical equipment mounted thereto comprising:
  a. a post having an interior configured to removably receive the pole;
  b. a first brace secured to the post and having first leg means for mounting at a first location to a selected member of a wheelchair; and
  c. a second brace slidable along the post for mounting at a second location to the selected member of the wheelchair, the first and second braces cooperating to mount the post in a generally vertical attitude,
  so that the intravenous related medical equipment and a patient connected thereto can be transported together by the wheelchair.

9. The bracket of claim 8 further comprising stop means for limiting the amount of insertion of the pole into the bracket post.

10. The bracket of claim 9 further comprising lock means for locking the pole in the bracket post when the pole is inserted into the bracket post.

11. The bracket of claim 8 wherein the first and second braces are of unequal lengths to thereby enable the bracket to accommodate a contoured wheelchair and maintain the post in a generally vertical attitude.

* * * * *